US007345117B1

(12) United States Patent
Barbucci et al.

(10) Patent No.: US 7,345,117 B1
(45) Date of Patent: Mar. 18, 2008

(54) SULPHATED HYALURONIC ACID AND SULPHATED DERIVATIVES THEREOF COVALENTLY BOUND TO POLYURETHANES, AND THE PROCESS FOR THEIR PREPARATION

(76) Inventors: Rolando Barbucci, Via Primo Simi 1, 53010 Lucignano d'Arbia (IT); Marco Consumi, S. Eugenia 83, 53100 Siena (IT); Agnese Magnani, LocalitàAgresto 391, 53010 S. Rocco a Pilli (IT); Lanfranco Callegaro, Via Monte Grappa 6, 36016 Thiene (IT)

( * ) Notice: Subject to any disclaimer, the term of this patent is extended or adjusted under 35 U.S.C. 154(b) by 0 days.

(21) Appl. No.: 09/622,146

(22) PCT Filed: Feb. 24, 1999

(86) PCT No.: PCT/EP99/01191

§ 371 (c)(1),
(2), (4) Date: Jan. 2, 2001

(87) PCT Pub. No.: WO99/43728

PCT Pub. Date: Sep. 2, 1999

(30) Foreign Application Priority Data

Feb. 25, 1998 (IT) ............................... PD98A0037

(51) Int. Cl.
C08F 283/04 (2006.01)
C08G 18/34 (2006.01)
C08G 18/46 (2006.01)
A61L 31/06 (2006.01)
A61L 31/10 (2006.01)

(52) U.S. Cl. ................ 525/454; 424/78.17; 424/78.37; 514/54; 527/300; 527/301; 528/49; 528/71; 536/122; 536/123.1; 536/126

(58) Field of Classification Search ................ 525/454; 528/49, 71; 424/78.17, 78.37; 514/54; 527/300, 527/301; 536/122, 123.1, 126
See application file for complete search history.

(56) References Cited

U.S. PATENT DOCUMENTS

| 4,487,865 | A | | 12/1984 | Balazs et al. ................. 524/29 |
|---|---|---|---|---|
| 4,500,676 | A | * | 2/1985 | Balazs et al. ............ 428/425.1 |
| 4,851,521 | A | * | 7/1989 | della Valle et al. ........ 536/55.1 |
| 4,944,767 | A | | 7/1990 | Barbucci et al. ............... 623/66 |
| 5,023,114 | A | * | 6/1991 | Halpern et al. ............. 427/338 |
| 6,027,741 | A | * | 2/2000 | Cialdi et al. ................. 424/422 |
| 6,040,415 | A | * | 3/2000 | Arimori et al. ............... 528/71 |
| 6,051,701 | A | * | 4/2000 | Cialdi et al. ................. 536/123 |
| 6,160,032 | A | * | 12/2000 | Shah et al. ................. 523/112 |
| 6,339,074 | B1 | * | 1/2002 | Cialdi et al. .................. 514/54 |
| 6,579,978 | B1 | * | 6/2003 | Renier et al. ................. 536/53 |
| 6,734,298 | B1 | * | 5/2004 | Barbucci et al. ........... 536/55.1 |
| 6,831,172 | B1 | * | 12/2004 | Barbucci et al. .............. 536/53 |
| 6,833,363 | B2 | * | 12/2004 | Renier et al. ................. 514/54 |

FOREIGN PATENT DOCUMENTS

| WO | 9525751 | | 9/1995 |
|---|---|---|---|
| WO | 96/24392 | * | 8/1996 |
| WO | 98/45335 | | 10/1998 |

OTHER PUBLICATIONS

Marconi W: "New Polyurethane Compositions High Amounts of Covalently Bonded Heparin", Chemistry and Physics, vol. 194, No. 5, May 1, 1993, pp. 1347-1356.
Biomaterials, vol. 18 No. 21, Pub. 1997, pp. 1411-1415, "Biocompatibility and Enzymatic Degadation Studies on Sulphated Hyaluronic Acid Derivatives", by Giovanni Abatangelo, Rolando Barbucci, Paola Brun and Stefania Lamponi.
Mackromol. Chem., 194, Pub. 1993, pp. 1347-1356, "New Polyurethane Compositions Containing High Amounts of Covalently Bonded Heparin", by Walter Marconi, Paolo Barontini, Andrea Martinelli, Antonella Piozzi.

* cited by examiner

Primary Examiner—Rabon Sergent

(57) ABSTRACT

The present invention relates to the synthesis of a haemocompatible polymer, consisting of a polyurethane bound covalently to sulphated hyaluronic acid. These sulfated derivatives have anticoagulative, non-thrombogenic, antiviral and anti-inflammatory properties. They also have the ability to inhibit platelet adhesion, aggregation and activation. The invention is particularly advantageous in resisting the enzyme hyaluronidase, therefore ensuring anti-coagulant activities for longer periods of time when compared to similar compounds. This biocompatible polymer material is well suited for surgical or other medicinal uses.

6 Claims, 2 Drawing Sheets

SULPHATED HYALURONIC ACID AND SULPHATED DERIVATIVES THEREOF COVALENTLY BOUND TO POLYURETHANES, AND THE PROCESS FOR THEIR PREPARATION

FIELD OF THE INVENTION

The present invention concerns a polyurethane covalently bound to sulphated hyaluronic acid or to its sulphated derivatives, the process for their preparation, and the haemocompatible materials comprising said polyurethane.

STATE OF THE ART

Considerable efforts have been made over the last few decades in the synthesis and surface modification of constantly new classes of polymers, in order to provide haemocompatible materials for the use in surgery.

Polyurethanes are widely used in biomedical applications because of their good mechanical and haemocompatible properties.

In order to enhance the latter property, molecules able to inhibit the coagulative process have been bound to the surface of polyurethane.

These substances are usually chosen from among those which can prevent platelet adhesion and aggregation, or block coagulation factors.

Heparin is one of the modifying agents used, and it can be bound to the polymer surface by both ionic bonds (U.S. Pat. No. 4,944,767) and covalent bonds (W. Marconi et al., *Makromol. Chem.* 194, 1347-1356, 1993).

These bonds can be achieved once the polymer surface has been chemically modified by introducing reactive groups such as carboxy, hydroxy and amino groups.

However, one of the main drawbacks to the use of heparin is its high degradation rate on account of the enzyme heparinase, which limits its possible applications in fields of surgery such as cardiovascular surgery, which may call for the implant of devices where the absence of thrombogenicity must be guaranteed for lengthy periods.

Other modifying agents with anticoagulant properties are O-sulphated hyaluronic acid and its O-sulphated derivatives, prepared according to the method described in the international patent application by the Applicant, No. WO 95/25751.

Also of considerable importance are N-sulphated hyaluronic acid and its N-sulphated derivatives, optionally salified, wherein the glucosamines are partially N-sulphated or partially N-sulphated and partially or totally O-sulphated in position 6, as described in the international patent application by the Applicant No. WO 98/45335.

These sulphated derivatives have anticoagulative, nonthrombogenic, antiviral and anti-inflammatory properties, and it has been demonstrated that they inhibit platelet adhesion, aggregation and activation.

Moreover, the sulphated derivatives prove particularly advantageous in resisting the enzyme hyaluronidase, and they therefore ensure anticoagulant activity for far longer than heparin (G. Abatangelo et al., *Biomaterials* 18, 1997, 1411-1415). However, not all the above derivatives as such cannot be processed in the form of biomaterials because the higher is the percentage of sulphation, the greater is their hydrophilia.

Therefore the need of novel bio- and haemocompatible compounds, which also have the advantageous properties of the sulphated hyaluronic acid and derivatives thereof, and can be used as such for the preparation of biomaterials and for the coating of biomedical objects, is deeply felt.

SUMMARY OF THE INVENTION

The present invention relates to polymers with a high degree of biocompatibility and haemocompatibility, constituted by a polyurethane bound covalently to a sulphated hyaluronic acid and derivatives thereof.

Said polymers maintain the mechanical characteristics (resistance to wear and tear, bending, elasticity, etc.) and the stability of polyurethane, also showing the anticoagulant activity, the effectiveness in inhibiting platelet adhesion, activation and aggregation, and the resistance to hyaluronidase of the sulphated hyaluronic acid and of the sulphated derivatives thereof.

Moreover, the derivatives according to the present invention, constituted by a polyurethane bound covalently to sulphated hyaluronic acid or its sulphated derivatives, show the considerable advantage of being easily mobilised on the polymer surface of biomedical objects, in most cases exploiting solubility in organic solvents.

Indeed, the surface of an object made of polymeric material can be treated with the organic solution of the derivative triggering solubilization of the outer layers of the polymer and, due to the subsequent evaporation of the solvent, the derivative adheres to the surface, merging with the polymer material of which the object is made.

In view of the foregoing the present invention further relates to haemocompatible materials containing the polyurethane bound covalently to the sulphated hyaluronic acid or sulphated hyaluronic acid derivatives.

The present invention further relates to industrial or medical articles or devices coated with haemocompatible materials comprising the polyurethane bound covalently to the sulphated hyaluronic acid or sulphated hyaluronic derivatives.

DETAILED DESCRIPTION OF THE INVENTION

Figure 1:
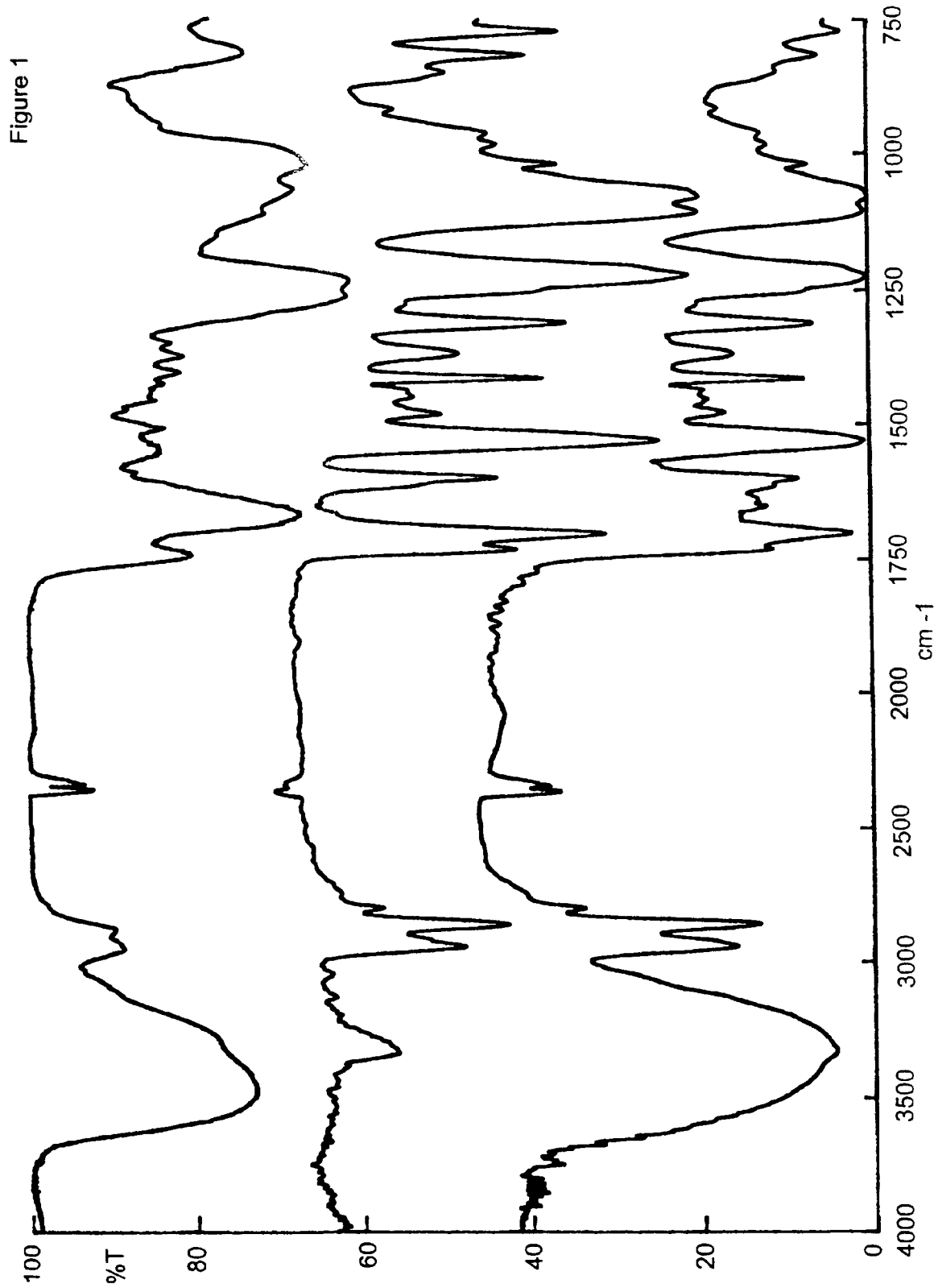
FIG. 1 shows the infra-red spectra of the O-sulphated hyaluronic acid with a degree of sulphation of 3.5, and of its polyurethane derivative in the dry and wet forms, as obtained in Example 1.

By sulphated hyaluronic acid and sulphated hyaluronic acid derivatives, we mean:

$A_1$) O-sulphated hyaluronic acid, and $A_2$) O-sulphated hyaluronic acid derivatives, both types being disclosed in U.S. Pat. No. 6,051,701, which is incorporated herewith by reference;

$B_1$) N-sulphated hyaluronic acids, and $B_2$) N-sulphated hyaluronic acid derivatives, both types being obtainable by means of a controlled sulphation reaction on the amino group of glucosamine of hyaluronic acid, previously deacetylated according to the procedure described by P. Shaklee (1984) Biochem. J., 217, 187-197. The reaction proceeds as illustrated below:

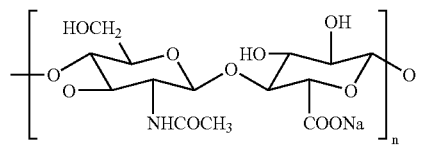

↓ De-N-acetylation

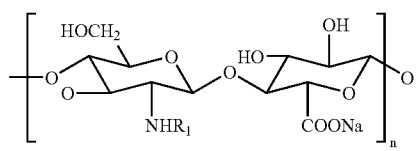

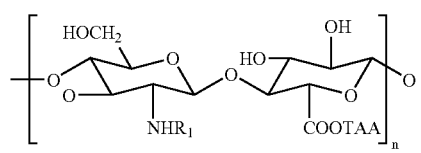

↓ R1-N-sulphation

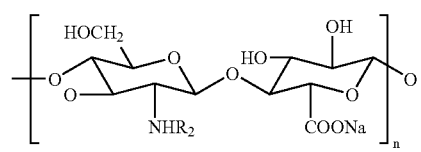

n: from 12 to 12,500

$R_1$=H, $COCH_3$

TAA=tetra-alkylammonium $R_2$=$SO_3$, $COCH_3$

Diagram 1 b) and c) mean the products of the chemical reaction illustrated in Diagram 1, wherein, besides the amino group of glucosamine, the primary hydroxy function of the same residue is also totally or partially involved in the sulphation reaction, as illustrated below:

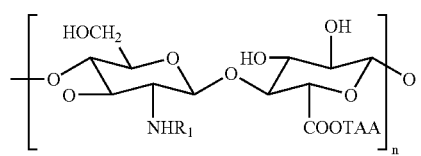

↓ N-sulphation
6-O-sulphation

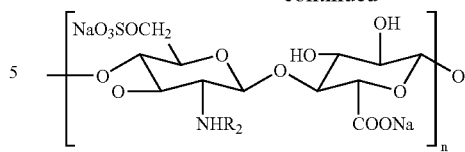

n: from 12 to 12,500

$R_1$=H, $COCH_3$

TAA=tetra-alkylammonium $R_2$=$SO_3$, $COCH_3$

Diagram 2

The derivatives generated according to diagrams 1 and 2 can be used as intermediate reactants in the preparation of compounds, according to the procedure described in U.S. Pat. No. 4,851,521, wherein the carboxy function of the glucuronic residue of hyaluronic acid, partially 2-N-sulphated or partially 2-N-sulphated and partially or totally 6-O-sulphated, is partially or completely reacted with alcohols of the aliphatic, aromatic, arylaliphatic, cycloaliphatic, heterocyclic series, producing the respective partial or total esters:

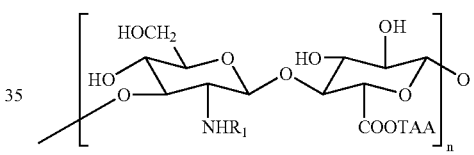

↓

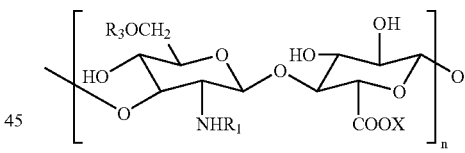

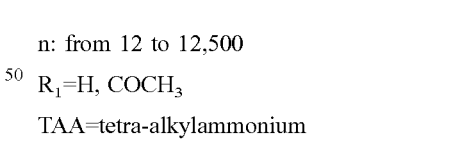

n: from 12 to 12,500

$R_1$=H, $COCH_3$

TAA=tetra-alkylammonium $R_2$=$SO_3$, $COCH_3$ $R_3$=$SO_3$, H

X=alcoholic residue, Sodium

Diagram 3

Moreover it is possible to use the synthetic derivatives according to diagrams 1 and 2 as intermediates in the preparation of crosslinked compounds, according to the procedures described in U.S. Pat. No. 5,676,964 and U.S. Pat. No. 4,957,744 respectively, wherein a part or all of the carboxy groups belonging to the D-glucosamine residue are reacted: i) using condensing agents with the alcoholic functions of the same polysaccharide chain or other chains, generating inner (or lactone) esters and intermolecular esters; ii) with polyalcohols of the aliphatic, aromatic, arylaliphatic, cycloaliphatic, heterocyclic series, generating crosslinking by means of spacer chains.

The above said sulphated compounds obtained according to the process of the present invention can be optionally salified with heavy metals, the heavy, metals being selected from the group of metal elements in the $4^{th}$, $5^{th}$ and $6^{th}$ periods of the periodic table, such as silver, iron, cobalt, copper, zinc, arsenic, strontium, zirconium, antimony, gold, cesium, tungsten, selenium, platinum, ruthenium, bismuth, tin, titanium and mercury.

In the O-sulphated derivatives of hyaluronic acid or hyaluronic acid derivatives of class $A_1$ and $A_2$ the number of O-sulphated groups is generally comprised between 0.5 and 3.5.

In the N-sulphated hyaluronic acid $B_1$ or in the N-sulphated hyaluronic acid derivatives $B_2$ the glucosaminic portions of the repeating unit may be:

a) partially N-sulphated, b) partially N-sulphated and partially O-sulphated, or c) partially N-sulphated and totally O-sulphated, wherein:

a) means a product obtained by means of a controlled sulphation reaction of the previously deacylated amino groups of glucosamine, b) and c) mean a product obtained by a sulphation reaction in which, besides the previously mentioned deacylated amino groups of glucosamine, also the primary hydroxy functions of the same residue are involved, partially or totally respectively.

The hyaluronic acid derivatives used to prepare the sulphated compounds of classes $A_2$ and $B_2$ are selected among
   the partial esters of hyaluronic acid containing at least one free carboxylic function and the remaining carboxylic functions being esterified with alcohols of the aliphatic, aromatic, arylaliphatic, cycloaliphatic and heterocyclic series,
   the partial crosslinked esters containing at least one free carboxylic function and the remaining carboxylic functions being esterified with the alcoholic function of the same hyaluronic acid chain or of a different chain like those disclosed in U.S. Pat. No. 5,676,964, we incorporate herewith by reference,
   the partial crosslinked esters disclosed in U.S. Pat. No. 4,957,744 we incorporate herewith by reference containing at least one free carboxylic function and the remaining carboxylic functions reacted with a polyalcohol of the aliphatic, aromatic, arylaliphatic, heterocyclic series, and wherein a crosslinking is thereafter generated by means of spacer chains.

The process for the preparation of the compounds $B_1$ and $B_2$ mainly consists of two steps, the first involving the controlled deacetylation of the natural polysaccharide, and the second involving the specific sulphation reaction of the primary hydroxyl or free amino functions of glucosamine.

Fractions of hyaluronic acid from biological and fermentation sources, with a molecular weight of between 5,000 and 5,000,000 Da, preferably between 50,000 Da and 300,000 Da, are solubilized in hydrazine hydroxide with a purity of no less than 98%, in a concentration range of between 1 and 50 mg/ml, preferably between 5 and 25 mg/ml. This solution is then supplemented with hydrazine sulphate in a weight/volume concentration varying between 0.1 and 3%, preferably 1%. The reaction is conducted within a temperature range of 40 to 90° C., preferably 60° C., under agitation, for as long as it takes to reach the desired degree of N-deacetylation.

Table 1 hereafter reports the yield expressed as the percentage of free amino groups, in terms of time expressed as hours of reaction:

TABLE 1

| Test | Temperature (° C.) | Time (hours) | N-deacetylation (%)* |
|---|---|---|---|
| DAc 1** | 60° C. | 4 | 3 |
| DAc 2 | 60° C. | 8 | 5 |
| DAc 3 | 60° C. | 16 | 9 |
| DAc 4 | 60° C. | 24 | 14 |
| DAc 5 | 60° C. | 48 | 23 |
| DAc 6 | 60° C. | 72 | 36 |

*The percentage of N-deacetylation is determined according to the method of J. Riesenfeld (Analy. Bioch. 1990, vol. 188, pages 383-389).
**DAc + N-deacetylation The reaction is then stopped by precipitation with a polar solvent, preferably ethanol. The precipitate is partially vacuum-dried and treated with a solution of iodic acid with a molarity range of between 0.1 and 1M, preferably 0.5M, and lastly, with iodohydric acid at a concentration of 57% (w/v). The pH of the solution is maintained between 5 and 7 by adding a solution of sodium acetate (10% w/v).

The aqueous phase containing the modified polysaccharide is extracted by repeated treatments with diethylether and then, once the yellow color has completely disappeared, the solution is treated again with ethanol.

The precipitate which forms, after further drying at 40° C., is solubilized in water at a concentration of between 10 ng/ml and 40 ng/ml, preferably 25 ng/ml, and the solution is percolated through a column containing an ion exchange resin activated with a tetra-alkylammonium hydroxide, where the alkyl residue of the quaternary ammonium is constituted by a chain of between 1 and 4 carbon atoms; tetrabutyl-ammonium hydroxide is preferably used.

The percolated product, represented by the quaternary ammonium salt of the modified polysaccharide, is then freeze-dried.

Preparation of: a) Partially N-Sulphated Derivative (Method A)

The quaternary ammonium salt, preferably of tetrabutyl-ammonium, of the partially deacetylated polysaccharide, is solubilized in a polar a solvent such as dimethyl sulphoxide, dimethyl formamide, dimethyl acetamide, N-methyl-pyrrolidone, preferably dimethyl formamide (DMFA), at a concentration of between 5 and 50 mg/ml (preferably 25 mg/ml).

The organic solution is supplemented with another solution obtained by a sulphating complex constituted by dimethylformamide sulphotrioxide (DMFA-$SO_3$), in DMFA, at a concentration varying between 50 and 200 mg/ml and preferably 100 mg/ml. The quantity of complex to be used, expressed in moles of $SO_3$, proves surprisingly to be equivalent to the moles of amino groups released by the N-deacetylation reaction.

The sulphation reaction proceeds at a temperature of between 0° and 20° C., preferably 4° C., for no longer than 45 hours and is then stopped by adding cold, distilled water.

The reaction solvent is first purified by precipitating the partially N-sulphated hyaluronic acid with ethanol and then dialyzing the resolubilized product with distilled water.

Lastly, the solution is freeze-dried and the solid product thus obtained undergoes chemical-analytical characterization to determine the degree of N-sulphation and the mean molecular weight (Table 2).

TABLE 2

| Test | % deacetylation | % N-sulphation | mean MW (Da) |
|---|---|---|---|
| HA | 0 | 0 | 165,000 |
| HA-NS1 | 5.0 (DAc2) | 4.8 | 157,000 |
| HA-NS2 | 14.2 (DAc4) | 13.9 | 147,000 |
| HA-NS3 | 23.5 (DAC5) | 23.0 | 139,000 |
| HA-NS4 | 36.1 (DAc6) | 34.2 | 124,000 |

HA = hyaluronic acid
HA-N-S = N-sulphated hyaluronicacid

Preparation of: b) Partially 2-N-Sulphated Derivative (Method B)

The quaternary ammonium salt, preferably of tetrabutylammonium, of the partially N-deacetylated polysaccharide is solubilized in a polar solvent such as dimethylsulphoxide, dimethylformamide, dimethylacetamide, N-methyl-pyrrolidone, preferably dimethylformamide (DMFA), at a concentration of between 54 and 50 mg/ml, preferably 30 mg/ml.

The organic solution is supplemented with another solution obtained by solubilizing the sulphating complex constituted by dimethylformamide sulphotrioxide (DMFA-$SO_3$), in DMFA, at concentrations varying between 50 and 200 mg/ml and preferably 100 mg/ml. The quantity of complex used, expressed as moles of $SO_3$ prove surprisingly to be equivalent to the moles of amino groups released by the N-deacetylation reaction.

The sulphation reaction proceeds at a temperature of between 0° and 20° C., preferably at 4° C. for 4 hours. A solution prepared by solubilizing the pyridine-sulfotrioxide complex in dimethylsulphoxide in such a quantity that the ratio between the moles of $SO_3$ of the sulphating agent and the moles of —$CH_2OH$ is between 1.1 and 1.3. Larger quantities of reagent may favor any substitution reactions in other alcohol groups (secondary) of the polysaccharide chain.

The reaction the proceeds for another 16 hours at least after which it is stopped by adding cold distilled water.

All subsequent steps concerning the purification of the modified polysaccharide are those described in Method A.

The analytical characterization performed on the derivatives obtained confirmed that the sulphation method proves surprisingly not only to substitute all the amino groups obtained by the partial deacetylation, but also results in the complete substitution of the primary alcohol group of the glucosamine residue of hyaluronic acid (Table 3).

TABLE 3

| Test | % N-deacetylation | % N-sulphation | % 6-O-sulphation |
|---|---|---|---|
| HA-N-OS1 | 5.0 (DAc 2) | 4.8 | 100 |
| HA-N-S1 | 14.2 (DAc 4) | 13.9 | 99.2 |
| HA-N-O-S1 | 23.5 (DAc 5) | 23.0 | 98.9 |
| HA-N-O-S1 | 36.1 (DAc 6) | 34.2 | 96.5 |

Moreover, by varying the molar quantities of the pyridine-$SO_3$ complex according to the primary hydroxyl groups (molar ratio of between 0.1 and 1), Method B enables a series of partially 2-N-sulphated and partially 6-O-sulphated derivatives to be obtained.

Any biocompatible polyurethane may be used for preparing the polyurethane bound covalently to sulphated hyaluronic acid. Preferred is the polyurethane present on the market with the trademark Pellethane®; particularly preferred is the polyurethane having an average molecular weight of 180000 Da, this polymer containing the repeating unit 4,4'-methylenebis (phenyl isocyanate).

The haemocompatible materials according to the present invention besides polyurethane bound covalently to sulphated hyaluronic acid may optionally further contain natural, synthetic or semisynthetic polymers and/or pharmaceutically active substances.

The pharmaceutically active substances that can be used are, for example, antibiotics, anti-infective, antimicrobial, antiviral, cytostatic, antitumoral, anti-inflammatory and wound healing agents, anaesthetics, cholinergic or adrenergic agonists and antagonists, antithrombotic, anticoagulant, haemostatic, fibrinolytic, thrombolytic agents, proteins and their fragments, peptides, polynucleotides, growth factors, enzymes and vaccines.

Among the natural polymers, it is possible to use, for example, collagen, coprecipitates of collagen and glycosamino glycans, cellulose, polysaccharides in the form of gels such as chitin, chitosan, pectin or pectic acid, agar, agarose, xanthane, gellan, alginic acid or alginates, polymannan or polyglycans, starch and natural gums.

The semisynthetic polymers, for example, can be chosen from the group consisting of collagen crosslinked with agents such as aldehydes or precursors of the same, dicarboxylic acid or the halides thereof, diamines, derivatives of cellulose, hyaluronic acid, chitin or chitosan, gellan, xanthane, pectin or pectic acid, polyglycans, polymannan, agar, agarose, natural gum and glycosamino glycans.

Lastly, among the synthetic polymers it is possible to use, for example, polylactic acid, polyglycolic acid or copolymers of the same or their derivatives, polydioxanes, polyphosphazenes, polysulphonic resins and PTFE.

The haemocompatible materials according to the present invention are preferably in the form of sponges, films, membranes, threads, tampons, non-woven fabrics, microspheres, nanospheres, gauzes, gels and guide channels.

The haemocompatible materials according to the present invention can be used in the cardiovascular field or in any application involving contact with the blood or with highly vascularised body tissues.

The above haemocompatible materials can be used to advantage in various surgical fields, in internal, osteoarticular, neurological, anastomotic, viscoelastic, ophthalmic, oncological, aesthetic, plastic, otorhinolaryngological, abdominal-pelvic, urogynaecological and cardiovascular surgery, in the prevention of post-surgical adhesions and in the prevention of hypertrophic scarring.

The haemocompatible materials according to the present invention can be used, besides in the surgical field, in haemodialysis, in cardiology, in dermatology, in opthalmology, in otorhinolaryngology, in dentistry, in gynaecology, in urology and in extracorporeal blood circulation and oxygenation.

The above haemocompatible materials in their various forms can also be used to advantage as cell culture supports, such as for mesenchymal cells or mature cells to obtain connective, glandular and nerve tissue.

The haemocompatible materials can also be used in the processes of preparation and coating of articles or devices to be used both in the medical field and in industry, which show, due to this coating, biological characteristics on the surfaces.

The objects that can be coated are, for example, catheters, guide channels, probes, cardiac valves, soft tissue prostheses, prostheses of animal origin such as cardiac valves from pigs, artificial tendons, bone and cardiovascular replacements, contact lenses, blood oxygenators, artificial kidneys, hearts, pancreases and livers, blood bags, syringes, surgical instruments, filtration systems, laboratory instruments, containers for cultures and for the regeneration of cells and tissues, supports for peptides, proteins and antibodies.

Particularly preferred polyurethane bound covalently to sulphated hyaluronic acid are those characterised by the following formula (I)

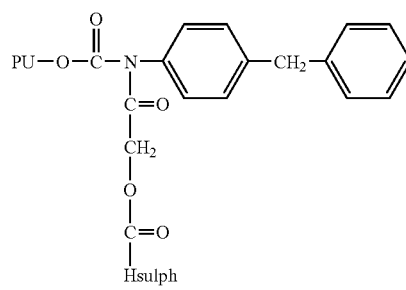

(I)

and formula (II)

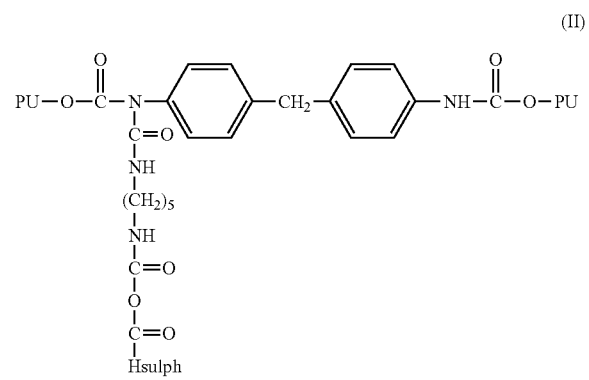

wherein PU is a residue of the polyurethane chain, and Hsulph is a residue of sulphated hyaluronic acid as in the above classes $A_1$ and $B_1$, or a sulphated hyaluronic acid derivative containing at least one free carboxylic function as in the above classes $A_2$ and $B_2$.

In particular, the process for preparing the polyurethane bound covalently to sulphated hyaluronic acid of formula (I) is obtained with a process comprising the following steps:

i) the polyurethane (IV) is reacted with bromoacetic acid (VII) in the presence of N,N'-dicyclohexylcarbodiimide (DCC), to obtain the adduct of formula (III) according to the following reaction scheme:

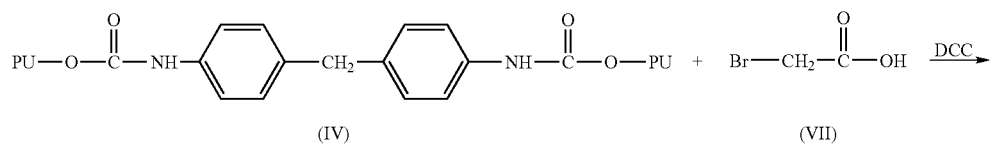

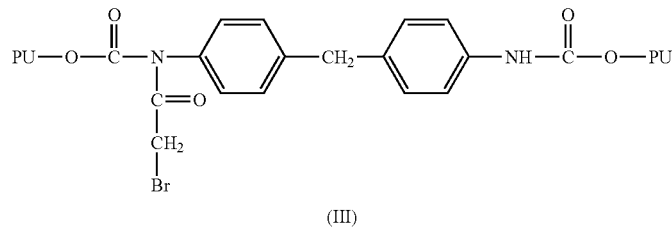

(III)

ii) the adduct (III) coming from step i) is reacted with HOOC-Hsulph wherein Hsulph has the above meanings, thereby obtaining the compound of formula (I) according to the following scheme:

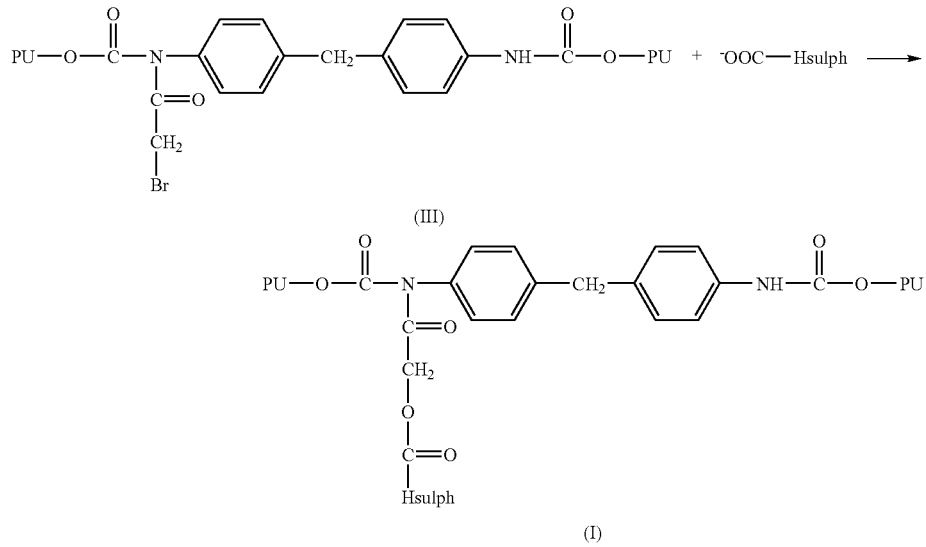

The reaction in step i) is typically carried out in an inert atmosphere and in an organic solvent, preferably in dimethylformamide (DMF).

Before carrying out step ii) the reaction mixture coming from step i) is preferably filtered to separate the solution containing the desired product (III) from the precipitate of dicyclohexylurea which forms simultaneously.

Step ii) is preferably carried out in the presence of sodium bicarbonate.

The reaction in step ii) is typically carried out in 24 hours at a temperature ranging from 25 to 45° C., and preferably at 25° C.

The polyurethane derivative of formula (II) can be obtained by a process comprising the following steps i') a sulphated hyaluronic acid or a sulphated hyaluronic acid derivative, wherein part or all of the carboxy groups of the glucuronic residue are in their acid form HOOC-Hsulph is reacted with hexamethylenediisocyanate (HMDI) (V), to obtain the adduct of formula (VI)

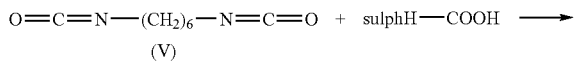

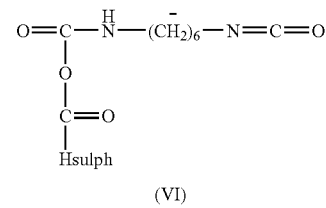

ii') the adduct (VI) coming from step i') is reacted with the polyurethane (IV) to obtain the desired product (II) according to the following scheme

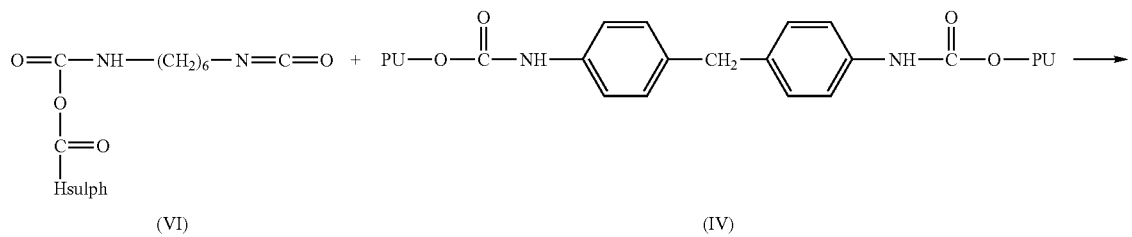

-continued

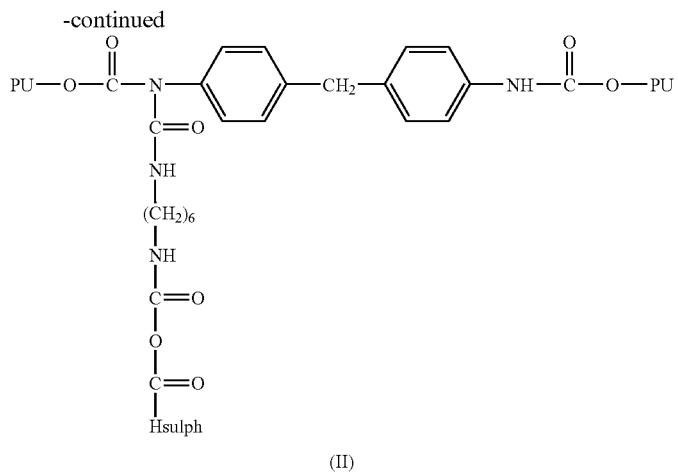

(II)

Both reactions in steps i') and ii') are typically carried out in an inert atmosphere, by using DMF as the solvent.

The temperature in step ii') is kept in the range from 45 to 55° C. for a time from 48 to 72 hours, while the mixture is left to react.

The following examples are given to provide non-limiting illustrations of the present invention.

EXAMPLE 1

Polyurethane Covalently Bound to O-Sulphated Hyaluronic Acid of Formula (I) (PUBRAC-1)

30 ml of a 10% (w/v) solution in DMF of Pellethane® are supplemented with 1.5 g of DCC while stirring.

Once the DCC has dissolved, 1.8 g of bromoacetic acid dissolved in a minimal quantity of DMF are added drop by drop.

After approximately 30 minutes the solution is filtered to separate it from the white dicyclohexylurea precipitate.

1 g of O-sulphated hyaluronic acid sodium salt (molecular weight 200 kDa and degree of sulphation 3.5) is dissolved in 60 ml of water, and this solution has percolated along the length of a ion exchange column, packed with 75 ml of a sulphonic resin in the form of tetrabutilammonium salt.

This resin has been prepared by the means of activation of a protonated sulphonic resin with a tetrabutilammonium hydroxide 40% w/v solution.

The solution containing the O-sulphated hyaluronic acid tetrabutilammonium salt coming from the column has been collected, then freeze dried.

200 mg of the so-obtained O-sulphated hyaluronic acid tetrabutilammonium salt and 2 g of sodium bicarbonate are added to the above polyurethane solution in DMF.

The mixture is left to react for 24 hours while being stirred at a temperature of 25° C.

If any precipitate has formed the reaction mixture is filtered again, then cast in Petri dishes.

We report hereafter in FIG. 1 the infra-red spectra of the sulphated hyaluronic acid with a degree of sulphation of 3.5, and of its polyurethane derivative in the dry and wet forms, obtained as above illustrated.

The polyurethane derivative in its dry state presents the typical spectrum of polyurethane not modified with sulphated hyaluronic acid, whereas in its wet state, peaks of between 3600 and 2800 $cm^{-1}$ and at 1654 $cm^{-1}$ can be seen as relative to the functional groups of the sulphated hyaluronic acid.

EXAMPLE 2

Polyurethane Covalently Bound to N-Sulphated Hyaluronic Acid of Formula (I) (PUBRAC-2)

30 ml of a 10% (w/v) solution in DMF of Pellethane® are supplemented with 1.5 g of DCC under stirring.

Once the DCC has dissolved, 1.8 g of bromoacetic acid dissolved in a minimal quantity of DMF is added drop by drop.

30 to 40 minutes later, the solution is filtered to separate it from the white precipitate of dicyclohexylurea.

This solution is supplemented with 2 g of sodium bicarbonate and 200 mg of N-sulphated hyaluronic acid tetrabutilammonium salt obtained starting from N-sulphated hyaluronic acid sodium salt (molecular weight 200 KDa and 30% sulphation) as described in Example 1 for the corresponding O-sulphated compound.

The reaction mixture is then left to react for 24 hours under stirring at a temperature of 25° C.

It is filtered again, and then cast in Petri dishes.

EXAMPLE 3

Polyurethane Covalently Bound to O-Sulphated Hyaluronic Acid of Formula (I) (PUBRAC-3)

2 g of DCC are added in an inert atmosphere to 25 ml of a 10% (w/v) solution in DMF of Pellethane® while stirring.

Once the DCC has dissolved, 1.8 g of bromoacetic acid dissolved in a minimal quantity of DMF are added drop by drop.

After approximately 30 minutes the solution is filtered to separate it from the white precipitate of dicyclohexylurea.

To the so-obtained solution 250 mg of O-sulphated hyaluronic acid tetrabutilammonium salt, prepared starting from the corresponding sodium salt (molecular weight 200 KDa and degree of sulphation 3.5) as described above in Example 1, and 2 g of sodium bicarbonate are added, then the mixture is left to react for 24 hours while being stirred at a temperature of 45° C.

If any precipitate has formed the reaction mixture is filtered again, then cast in Petri dishes.

EXAMPLE 4

Purification of Polyurethane Covalently Bound to Sulphated Hyaluronic Acid of Formula (I) Obtained According to Example 3 (PUBRAC Ris THF)

The preparation procedure as described in Example 3 is carried out once again, but the reaction product is dissolved in THF before cast in Petri dishes.

EXAMPLE 5

Purification of Polyurethane Covalently Bound to Sulphated Hyaluronic Acid of Formula (I) Obtained According to Examples 1-4 (PUBRAC)

Before cast in Petri dishes, the reaction product as obtained in Examples 14 is first washed with acetone, then 2-3 washing with a 10% solution of NaCl are performed.

EXAMPLE 6

Polyurethane Covalently Bound to O-Sulphated Hyaluronic Acid of Formula (II) (PUHMDI-6)

O-sulphated hyaluronic acid is obtained starting from the corresponding sodium salt (molecular weight 200 kDa and degree of sulphation 3.5) as described above in Example 1, and a complete protonation of its carboxy group is performed bringing the tetrabutilammonium salt solution coming from the column to pH=3-4, before freeze drying.

300 mg of the so-obtained O-sulphated hyaluronic acid are dissolved in the minimal quantity of DMF (approximately 10 ml).

Once solubilization is complete, the solution is placed in a flask containing 200 µl of HMDI under stirring and in an inert atmosphere.

30 minutes later, 10 ml of a 10% (w/v) Pellethane® solution in DMF are added.

The solution is left under stirring and in an inert atmosphere at a temperature of 45-50° C. for 3 days. It is then cast in Petri dishes.

EXAMPLE 7

Polyurethane Covalently Bound to O-Sulphated Hyaluronic Acid of Formula (II) (PUHMDI-7)

O-sulphated hyaluronic acid is obtained starting from the corresponding sodium salt (molecular weight 200 kDa and degree of sulphation 3.5) as described above in Example 1, and a complete protonation of its carboxy group is performed bringing the tetrabutilammonium salt solution coming from the column to pH=34, before freeze drying.

250 mg of the so-obtained O-sulphated hyaluronic acid are dissolved in the minimal quantity of DMF (approximately 10 ml), then the solution is poured under stirring and in an inert atmosphere into a flask containing 20011 of HMDI.

30 minutes later, 25 ml of a 10% (w/v) solution in DMF of Pellethane® are added to the reaction mixture preserving an inert atmosphere.

The solution is left under stirring and in an inert atmosphere at a temperature of 55° C. for 48 hours. It is then cast in Petri dishes.

EXAMPLE 8

Purification of Polyurethane Covalently Bound to O-Sulphated Hyaluronic Acid of Formula (II) Obtained According to Examples 6 and 7 (PUHMDI)

Before cast in Petri dishes, the reaction product as obtained in Examples 6 and 7 is washed with a 10% solution of NaCl for 2-3 times.

EXAMPLE 9

Test of Platelet Adhesion on the Material Obtained According to Example 1 (PUBRAC-1)

Blood was drawn from a healthy, non-smoking donor who had taken no drugs for a fortnight before. Platelet-rich plasma (PRP) was obtained by centrifuging the whole blood at 250 rpm for 25 minutes at room temperature.

1 ml of PRP was placed in contact with each sample (0.5 cm×0.5 cm) of the test polymer and these were then left for 3 hours at room temperature in order to favour platelet adhesion. The samples were then washed in PBS (phosphate buffer solution) to remove any platelets which had not adhered to the surface, and then incubated in a solution of glutaraldehyde at 2.5% (v/v) in 100 mM sodium cacodylate for 30 seconds.

Subsequently, the films were washed in cacodylate of sodium, 100 mM, for 30 seconds, rinsed in distilled water and left in the first dehydrating solution (70% v/v of ethanol in distilled water) for 15 minutes. The samples were then transferred to the second dehydrating solution (90% v/v of ethanol in distilled water) for 15 minutes and lastly in absolute ethanol for another 15 minutes.

Figure 2:
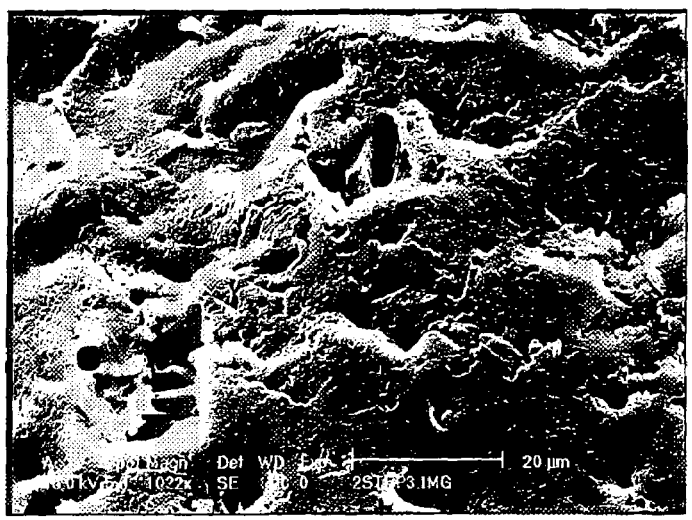
FIGS. 2, 3 and 4 show the SEM (Scanning Electron Microscope; magnification=1022×) images of the platelet adhesion test on the polyurethane derivative of O-sulphated hyaluronic acid obtained in Example 1.
Figure 3:
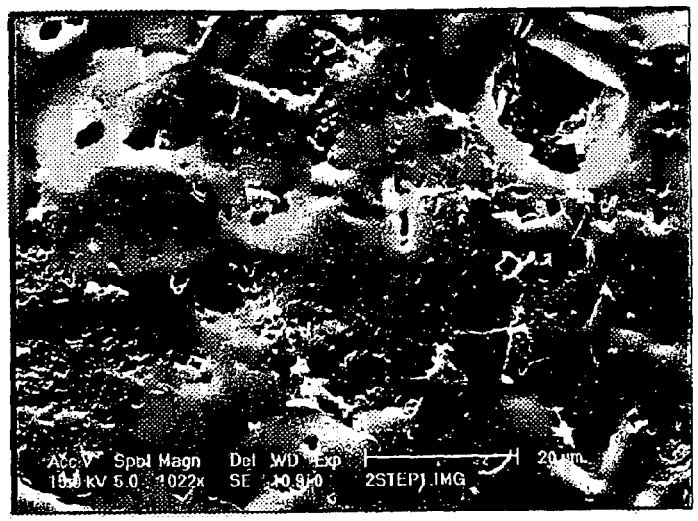
Figure 4:
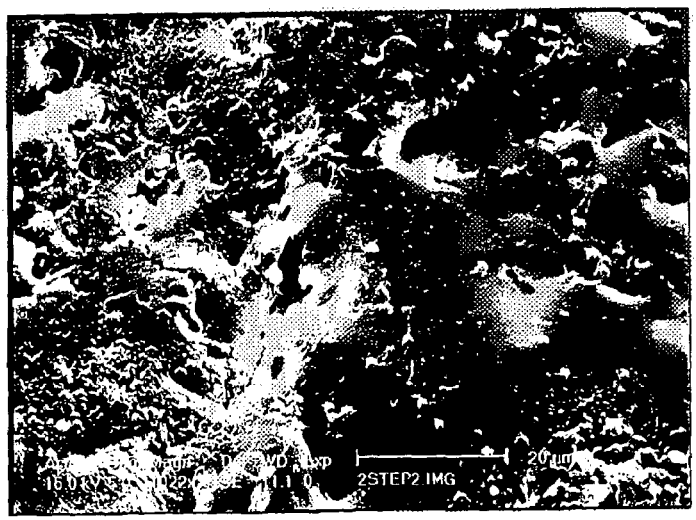

All the samples were then dehydrated in a vacuum for 12 hours, metallized with gold and analysed with a scanning electron microscope (SEM) (FIGS. 2, 3 and 4).

As can be seen from FIGS. 2, 3 and 4, the surface of the material is morphologically irregular and characterised by the presence of numerous slits of varying sizes. Despite these irregularities, 90% of the material presents no phenomena of platelet adhesion.

Only on the remaining 10% of the surface can the presence of platelets be observed, which in some cases form small clusters while in others they appear to maintain their individual character even though they have lost the discoid shape typical of non-activated platelets, and they have extruded pseudopods with which they cling to the surface.

EXAMPLE 10

Test of Whole Blood Coagulation on the Material Obtained According to Examples 3 (PUBRAC-3) and 4 (PUBRAC Ris THF)

This test was performed on PUBRAC-3 and PUBRAC Ris THF using blood from a single donor.

5 ml of blood was placed in contact with a sample (0.5 cm×0.5 cm) of the following materials

| | |
|---|---|
| control | polystyrene |
| PU | Pellethane® |
| PUBRAC-3 | polyurethane derivative according to Example 3 |
| PUBRAC Ris THF | polyurethane derivative according to Example 4 |

The samples were left at room temperature and the time necessary to achieve blood coagulation is then measured.
The results are reported in the following table:

TABLE 1

| SAMPLE | COAGULATION TIME (minutes) |
|---|---|
| Control (polystyrene) | 25 ± 2 |
| PU | 26 ± 2 |
| PUBRAC-3 | >120 |
| PUBRAC Ris THF | >120 |

Table 1 shows that the polyurethane derivatives according to the present invention have an anticoagulant activity at least equal to that of polyurethane, and even much higher than that for the polyurethane derivative obtained according to Example, which shows a coagulation time getting over 2 hours.

EXAMPLE 11

Thrombin Time Measured by Using the Material Obtained According to Example 3 (PUBRAC-3) and 7 (PUHMDI-7)

The ability of the derivatives according to the present invention in increasing blood coagulation time is measured by the thrombin time test conducted with a coagulometer.

An assessment is made of the time it takes to transform fibrinogen into fibrin after the addition of an excess of thrombin in a blood sample in the presence of the polymer. A result of over 120 seconds is no longer significant.

The results are reported in the following table:

TABLE 2

| SAMPLES | THROMBIN TIME (seconds) |
|---|---|
| Control (polystyrene) | 12.1 ± 0.9 |
| PU | 12.5 ± 0.4 |
| PUBRAC-3 air side (Ø 0.8 cm) | >120 |
| PUBRAC-3 glass side (Ø 0.8 cm) | >120 |
| PUBRAC-3 glass side (0.8 cm × 0.5 cm)# | 26.2 ± 3.8 |
| PUBRAC-3 air side (0.8 cm × 0.5 cm)# | 15.2 ± 0.2 |
| PUHMDI-7 (0.8 cm × 0.5 cm) | 16.3 ± 0.2 | thrombin time determined on plasma after 10 minutes contact with the polyurethane derivative at 37° C.

The table shows that the anticoagulant activity occurs on the side of the film which is in contact with the glass because the polar environment causes the sulphated hyaluronic acid group to be exposed on the surface, while different results are observed on the side which is in contact with the air.

EXAMPLE 12

Reptilase Time Measured by Using the Material Obtained According to Examples 3 (PUBRAC-3) and 4 (PUBRAC Ris THF)

Reptilase, a fraction extracted from the venom of the South American snake Bothrox atrox, is an enzyme that clots fibrinogen by splitting off its fibrinopeptide A.

The reptilase time is determined by incubating 0.3 ml of human plasma on the round samples (diameter 0.8 cm) of PUBRAC-3 and PUBRAC Ris THF at 37° C. for 2 minutes, then adding Reptilase Reactive (function of thrombin extracts from Bothrox Atrox venom, Haemodiagnostica Diagnostica Stago, Boehringer Mannheim), and measuring the clotting time automatically (Elvi Digiclot 2 Coagulometer, Logos S.p.A., Milan, Italy). Table 3 shows the effects of the materials obtained according to Examples 3 and 4 on reptilase time.

TABLE 3

| SAMPLE | REPTILASE TIME |
|---|---|
| Control (polystyrene) | 16.20 ± 0.05 |
| PUBRAC-3 | 15.2 ± 0.2 |
| PUBRAC Ris THF | 16.65 ± 0.05 |

The data in Table 3 show that the materials obtained according to Examples 3 and 4 have moderate and not very significant effects on reptilase time.

EXAMPLE 13

Thrombin Inhibition Measured by Using the Material Obtained According to Example 3 (PUBRAC-3)

The thrombin inhibition in plasma and in the presence of purified molecules, i.e. antithrombin III (AT II) and heparin cofactor (HC II), were studied for the material as obtained in Example 3 (PUBRAC-3), in order to investigate the manner in which the derivatives of the present invention exert their anticoagulant activity. Selected donors were normal, healthy subjects who had fasted for more than 8 hours and had not taken any medication for at least 14 days.

Blood samples were drawn in 3.8% (w/v) tri-sodium citrate as anticoagulant at a ratio of 9 parts blood to 1 part citrate. The samples were centrifuged at 3500 rpm for 15 minutes to obtain platelet poor plasma (PPP). Pooled citrated plasma was prepared from 10-12 normal drug free volunteers and stored in aliquots at −80° C. AT III (1 U.I./ml) and HC II (Heparin Cofactor II purchased by Calbiochem, USA) were reconstituted from lyophilised powder with sterile water and used immediately. 32.4 mg of human fibrinogen (molecular weight≈341,000, Calbiochem, USA) was dissolved in 6 ml of a physiological solution (0.9% NaCl, pH=7.4), then 0.2 ml of this solution were placed in contact with a sample of PUBRAC-3 (Ø0.7 cm).

0.2 ml of AT III or 0.2 ml of HC II or 0.2 ml of PBS was then added to the above sample.

The thrombin time with or without AT III and HC II was determined manually by adding 0.2 ml of thrombin (Human Thrombin purchased by Boheringer Mannheim, Germany) to 0.2 ml of the above samples.

The results are summarised in the following table:

TABLE 4

| SAMPLE | Thrombin Time (sec.) without AT III and HC II | Thrombin Time (sec.) with AT III | Thrombin Time (sec.) with HC II |
|---|---|---|---|
| PU | 8.4 ± 0.4 | 8.1 ± 0.2 | 18.5 ± 1.3 |
| PUBRAC-3 | 67.3 ± 3.3 | 63.3 ± 3.3 | >120 |

The above experiment was performed both with and without AT III and the results obtained were approximately the same in both cases, thus demonstrating that presumably the inactivation of thrombin by the polyurethane derivatives of the present invention is not mediated by AT III.

Moreover, the above results show the ability of the present derivatives to accelerate the thrombin inhibition mediated by HC II.

In conclusion, the thrombin was inhibited by the present polyurethane derivatives both via HC II and via direct interaction.

The invention claimed is:

1. A process for preparing the polyurethane of formula (I)

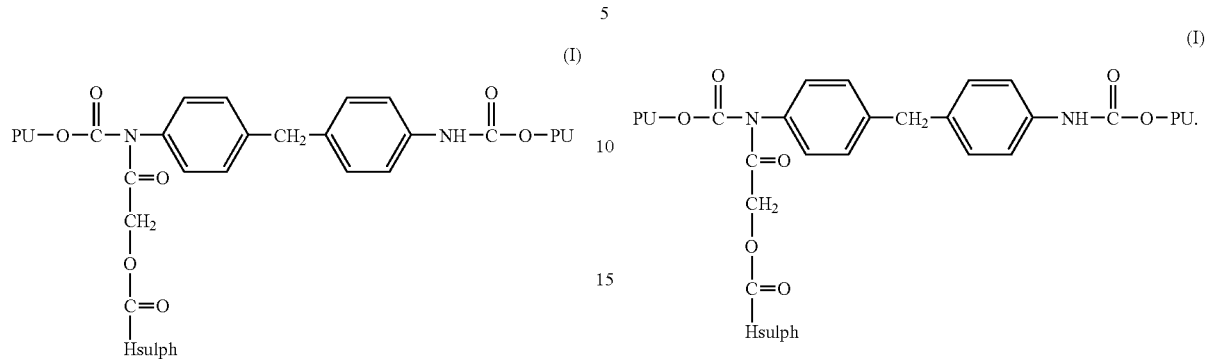

wherein PU is a residue of the polyurethane chain and Hsulph is a residue of an O-sulphated hyaluronic acid derivative containing at least one free carboxylic function comprising the following steps:

i) the polyurethane (IV) is reacted with bromoacetic acid (VII) in the presence of N,N'-dicyclohexylcarbodiimide (DCC), to obtain the adduct of formula (III)

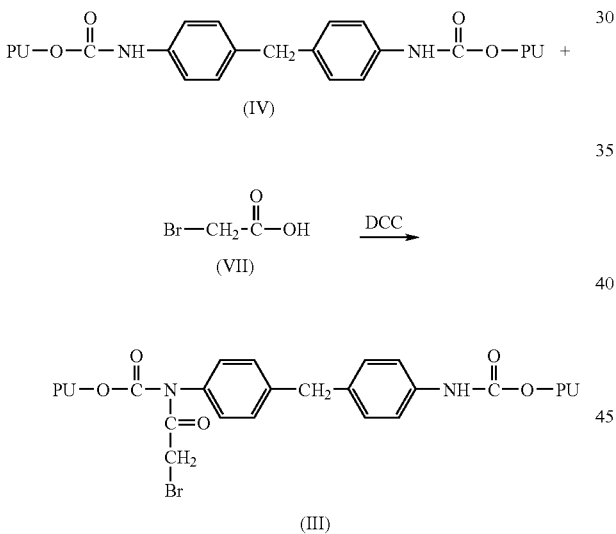

ii) the adduct (III) coming from step i) is reacted with HOOC-Hsulph, wherein Hsulph is defined as above, thereby obtaining the compound of formula (I)

2. The process according to claim 1, wherein the hyaluronic acid derivative used to prepare the said O-sulphated hyaluronic acid derivative is selected from the group consisting of:
   (a) partial esters of hyaluronic acid containing at least one free carboxylic function and any remaining carboxylic function esterified with an aliphatic, aromatic, arylaliphatic, cycloaliphatic or heterocyclic alcohol;
   (b) partial crosslinked esters containing at least one free carboxylic function and any remaining carboxylic functions being esterified with an alcoholic function of the same hyaluronic acid molecule or of a different hyaluronic acid molecule; and
   (c) partial crosslinked esters containing at least one free carboxylic function reacted with an aliphatic, aromatic, arylaliphatic or heterocyclic polyalcohol, and wherein crosslinking is thereafter generated by means of spacer chains.

3. The process according to claim 1, wherein the reaction in step i) is carried out in an inert atmosphere in dimethylformamide.

4. The process according to claim 1, wherein the reaction mixture coming from step i) is filtered before carrying out step ii), to separate the solution containing the adduct (III) from the precipitate of dicyclohexylurea which forms simultaneously.

5. The process according to claim 1, wherein step ii) is carried out in the presence of sodium bicarbonate.

6. The process according to claim 1, wherein the reaction in step ii) is carried out in 24 hours at a temperature of 25° C.

* * * * *